(12) United States Patent
Magno (10) Patent No.: US 11,331,107 B2
(45) Date of Patent: May 17, 2022

(54) MEDICAL DEVICE WITH REMOVABLE MOTOR

(71) Applicant: Gyrus ACMI, Inc., Southborough, MA (US)

(72) Inventor: Joey Magno, Cordova, TN (US)

(73) Assignee: Gyrus Acmi, Inc., Westborough, MA (US)

( * ) Notice: Subject to any disclaimer, the term of this patent is extended or adjusted under 35 U.S.C. 154(b) by 279 days.

(21) Appl. No.: 16/263,493

(22) Filed: Jan. 31, 2019

(65) Prior Publication Data
US 2020/0246020 A1    Aug. 6, 2020

(51) Int. Cl.
*A61B 17/16* (2006.01)
*A61B 17/32* (2006.01)
(Continued)

(52) U.S. Cl.
CPC .... *A61B 17/1628* (2013.01); *A61B 17/32002* (2013.01); *A61B 2017/00477* (2013.01); *A61M 1/741* (2021.05); *B25F 5/02* (2013.01)

(58) Field of Classification Search
CPC ............ A61B 17/1622; A61B 17/1626; A61B 17/1628; A61B 17/32002; A61B 2017/320024; A61B 2017/320028; A61B 2017/00477; A61B 18/1402; A61B 18/1482; A61B 18/149; A61B 17/2909; A61B 17/320016; A61B 2017/0046; A61B 2017/00464; A61B 2018/0091; A61B 2018/00916; A61B 2018/00958; A61B 2018/0231; A61B 1/0052; A61B 1/00112; A61B 1/00121; A61B 1/00119; (Continued)

(56) References Cited

U.S. PATENT DOCUMENTS 5,712,543 A * 1/1998 Sjostrom ............ A61B 17/1626
                                                       318/71
5,910,152 A   6/1999 Bays
(Continued)

FOREIGN PATENT DOCUMENTS

CN    111493983 A    8/2020
EP      0904742 A2    3/1999
(Continued)

OTHER PUBLICATIONS

"European Application Serial No. 20150635.9, Extended European Search Report dated Jun. 30, 2020", 9 pgs.
(Continued)

*Primary Examiner* — Kathleen S Holwerda
*Assistant Examiner* — Uyen N Vo
(74) *Attorney, Agent, or Firm* — Schwegman Lundberg & Woessner, P.A.

(57) ABSTRACT

An apparatus including a frame, where the frame includes a user handle, a motor receiving area, and a first aperture through the frame into the motor receiving area, where the motor receiving area is configured to removably receive a cannulated motor assembly therein; and a first seal located proximate the first aperture through the frame, where the first seal is configured to form a seal between the cannulated motor assembly and the frame when the cannulated motor assembly is in the motor receiving area.

20 Claims, 4 Drawing Sheets

(51) Int. Cl.
  *A61B 17/00* (2006.01)
  *B25F 5/02* (2006.01)
  *A61M 1/00* (2006.01)

(58) Field of Classification Search
  CPC ..... A61M 1/0039; A61M 1/0041; B25F 5/00; B25F 5/001; B25F 5/02
  See application file for complete search history.

(56) References Cited

U.S. PATENT DOCUMENTS

| | | | |
|---|---|---|---|
| 6,152,941 | A | 11/2000 | Himes et al. |
| 6,958,071 | B2 | 10/2005 | Carusillo et al. |
| 8,894,654 | B2 | 11/2014 | Anderson |
| 10,076,340 | B2 | 9/2018 | Belagali et al. |
| 2004/0059363 | A1 | 3/2004 | Alvarez et al. |
| 2005/0256512 | A1* | 11/2005 | Del Rio ................. A61C 1/185 606/1 |
| 2009/0270899 | A1 | 10/2009 | Carusillo et al. |
| 2010/0034605 | A1 | 2/2010 | Huckins et al. |
| 2011/0064978 | A1* | 3/2011 | McGahan .......... A61B 17/1622 429/61 |
| 2014/0155889 | A1* | 6/2014 | Edwards ............ A61B 18/1482 606/42 |
| 2014/0288536 | A1 | 9/2014 | Le et al. |
| 2015/0053737 | A1* | 2/2015 | Leimbach .............. A61B 90/03 227/175.1 |
| 2015/0182230 | A1* | 7/2015 | Belagali ................ A61B 17/14 606/82 |
| 2017/0202605 | A1* | 7/2017 | Shelton, IV ........ H01M 6/5044 |
| 2017/0281197 | A1 | 10/2017 | Thistle |

FOREIGN PATENT DOCUMENTS

| | | |
|---|---|---|
| EP | 3689277 A1 | 8/2020 |
| JP | 2020124494 A | 8/2020 |
| WO | WO-2007/008703 A2 | 1/2007 |
| WO | WO-2014/084983 A1 | 6/2014 |
| WO | WO-2014162495 A1 | 10/2014 |
| WO | WO-2016/138059 A1 | 9/2016 |
| WO | WO-2017163226 A1 | 9/2017 |

OTHER PUBLICATIONS

"European Application Serial No. 20150635.9, Response filed Feb. 5, 2021 to Extended European Search Report dated Jun. 30, 2020", 15 pgs.

"Japanese Application Serial No. 2020-013509, Notification of Reasons for Refusal dated Mar. 29, 2021", w/ English Translation, 7 pgs.

* cited by examiner

FIG.6

MEDICAL DEVICE WITH REMOVABLE MOTOR

BACKGROUND

Technical Field

The example and non-limiting embodiments relate generally to a device having a removable motor and, more particularly, to a medical device.

Brief Description of Prior Developments

A debrider is a medical instrument that has an outer blade and an inner blade located within the outer blade. During a surgical procedure, one or both of the blades are rotated and, via a cutting feature on one or both of the blades, material such as tissue, cartilage, bone, or the like can be shaved, cut, resected, abraded and/or removed. Cannulated motors, having a cannulated drive shaft, are also known as described in U.S. Patent Application Publication No. US 2004/0059363 A1 which is hereby incorporated by reference in its entirety.

SUMMARY

The following summary is merely intended to be exemplary. The summary is not intended to limit the scope of the claims.

In accordance with one aspect, an example embodiment is provided in an apparatus comprising a frame, where the frame comprises a user handle, a motor receiving area, and a first aperture through the frame into the motor receiving area, where the motor receiving area is configured to removably receive a cannulated motor assembly therein; and a first seal located proximate the first aperture through the frame, where the first seal is configured to form a seal between the cannulated motor assembly and the frame when the cannulated motor assembly is in the motor receiving area.

In accordance with another aspect, an example embodiment is provided in an apparatus comprising: a cannulated motor comprising a rotatable drive shaft, where the rotatable drive shaft comprises a conduit therethrough and a first end configured to removably connect a debrider tool thereto; and a motor assembly housing on the cannulated motor, where the motor assembly housing is configured to attach to a frame of a handpiece assembly, where the cannulated motor is configured to be removably inserted into a motor receiving area of the handpiece assembly with the motor assembly housing releasably retaining the cannulated motor with the handpiece assembly.

In accordance with another aspect, an example method comprises providing a frame comprising a user handle, a motor receiving area, and a first aperture through the frame into the motor receiving area, where the motor receiving area is configured to removably receive a cannulated motor assembly therein; and connecting a first seal to the frame proximate the first aperture, where the first seal is configured to form a seal between the cannulated motor assembly and the frame when the cannulated motor assembly is in the motor receiving area.

In accordance with another aspect, an example method comprises providing a cannulated motor, where the cannulated motor comprises a drive shaft having a conduit therethrough and a connector at a first end of the drive shaft configured to removably connect a debrider tool thereto; and providing a motor assembly housing on the cannulated motor; where the motor assembly housing comprises a latch configured to be contacted by a latch of a handpiece to releasably mount the motor assembly housing, with the cannulated motor, in a receiving area of the handpiece.

In accordance with another aspect, an example method comprises providing a handpiece, where the handpiece comprises a frame forming a motor receiving area, where the frame comprises a first aperture through the frame into the motor receiving area, and where the frame comprises a user handle; and inserting a cannulated motor assembly into the motor receiving area, where a seal is provided between the cannulated motor assembly and the handpiece, and where the cannulated motor assembly is removably retained to the handpiece by a movable latch.

BRIEF DESCRIPTION OF THE DRAWINGS

The foregoing aspects and other features are explained in the following description, taken in connection with the accompanying drawings, wherein.

DETAILED DESCRIPTION OF EMBODIMENTS

Figure 1:
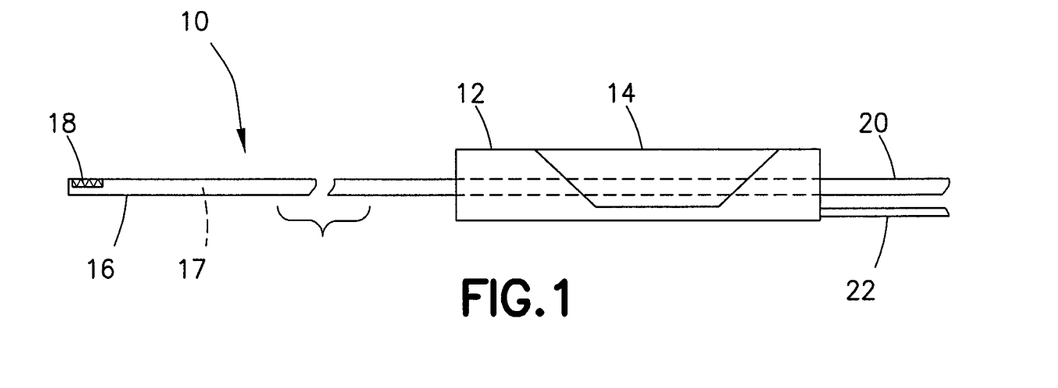
FIG. 1 is a schematic side view of an example embodiment of an apparatus comprising some features as described herein.

Referring to FIG. 1, there is shown a schematic side view of an apparatus 10 incorporating features of an example embodiment. Although the features will be described with reference to the example embodiments shown in the drawings, it should be understood that features can be embodied in many alternate forms of embodiments. In addition, any suitable size, shape or type of elements or materials could be used.

The apparatus 10, in this example embodiment, is a medical device and, more particularly, a debrider or a microdebrider. However, features as described herein may be used with other types of devices. The apparatus generally comprises a disposable handpiece assembly 12, a reusable cannulated motor assembly 14 and a removable/disposable surgical tool 16. In this example the surgical tool 16 is used as a debrider and comprises an outer blade and an inner blade located within the outer blade. During a surgical procedure, one or both of the blades 18 are axially rotated by the motor of the cannulated motor assembly 14. A cutting feature on one or both of the blades 18 is, thus, able to shave, cut, resect, abrade and/or removed tissue, cartilage, bone, or the like. The surgical tool 16 has a general tubular shape along its length to provide a conduit or channel 17 therethrough. This conduit or channel 17 is provided through the surgical tool 16 to allow the material cut from the patient and fluids to be suctioned through the apparatus 10 away from the site of the surgery. A suction conduit 20 is attached to a proximal end of the handpiece assembly 12. As further described below, the handpiece assembly 12 and the cannulated motor assembly 14 have conduits to connect the tool conduit 17 to the suction conduit 20. The apparatus 10 also comprises a cable 22 comprising electrical conductors attached to a proximal end of the handpiece assembly 12. The cable 22 can provide power and signals to the cannulated motor assembly 14 as further described below.

Figure 2:
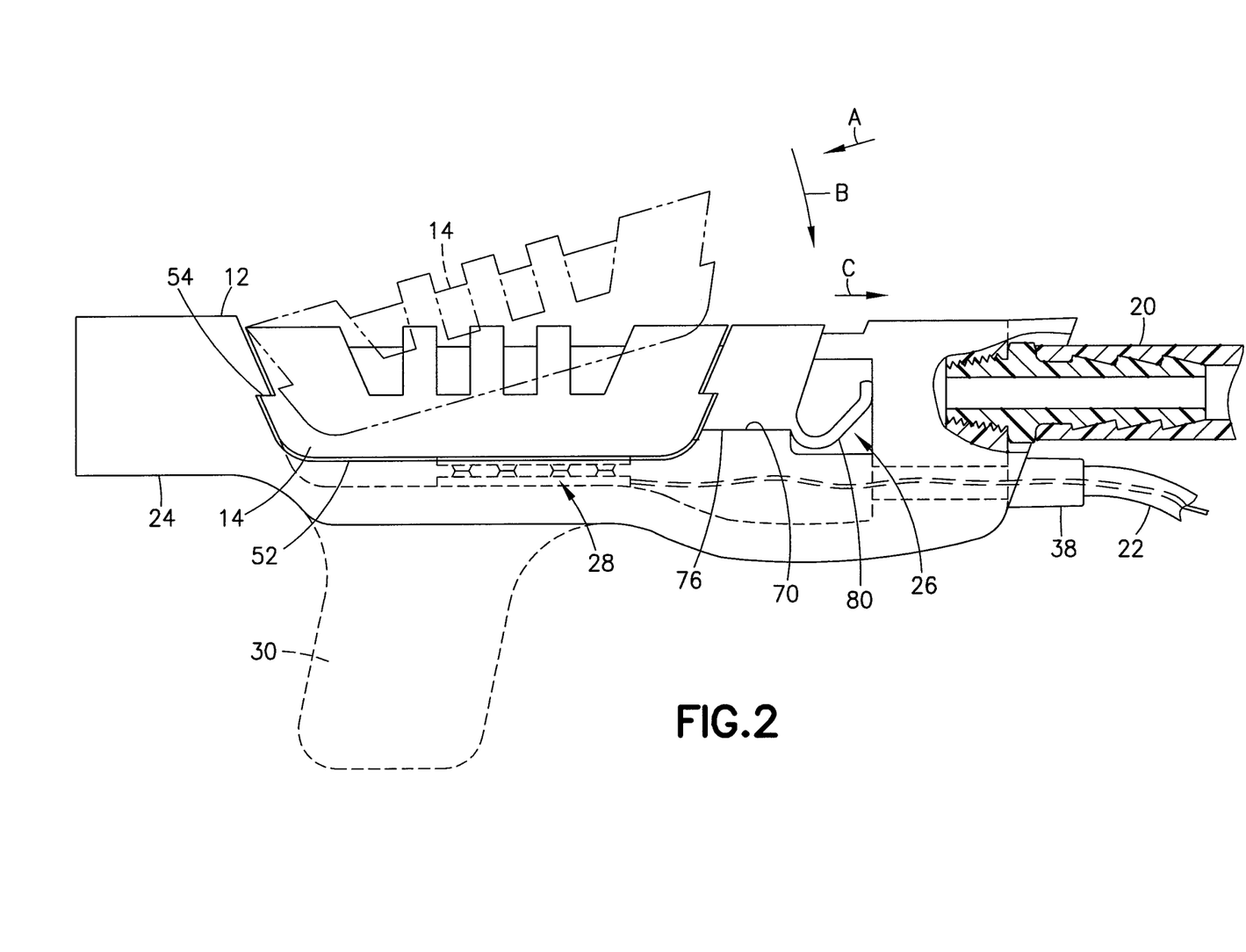
FIG. 2 is an enlarged side view of some of the components of the apparatus shown in FIG. 1.

Referring also to FIG. 2, the cannulated motor assembly 14 is removably connected to the handpiece assembly 12. In particular, in this example embodiment the handpiece assembly 12 and the cannulated motor assembly 14 are configured to allow the cannulated motor assembly 14 to be inserted into the top of the handpiece assembly 12, as illustrated by the arrows A and B as well as the dotted indication of 14, and then latched at a fixed location in the handpiece assembly 12. The latching engagement is releasable to allow the cannulated motor assembly 14 to be subsequently removed from the handpiece assembly 12. The cannulated motor assembly 14 may be cleaned separately from the handpiece assembly 12, and the handpiece assembly 12 may be disposable after use.

Figure 3:
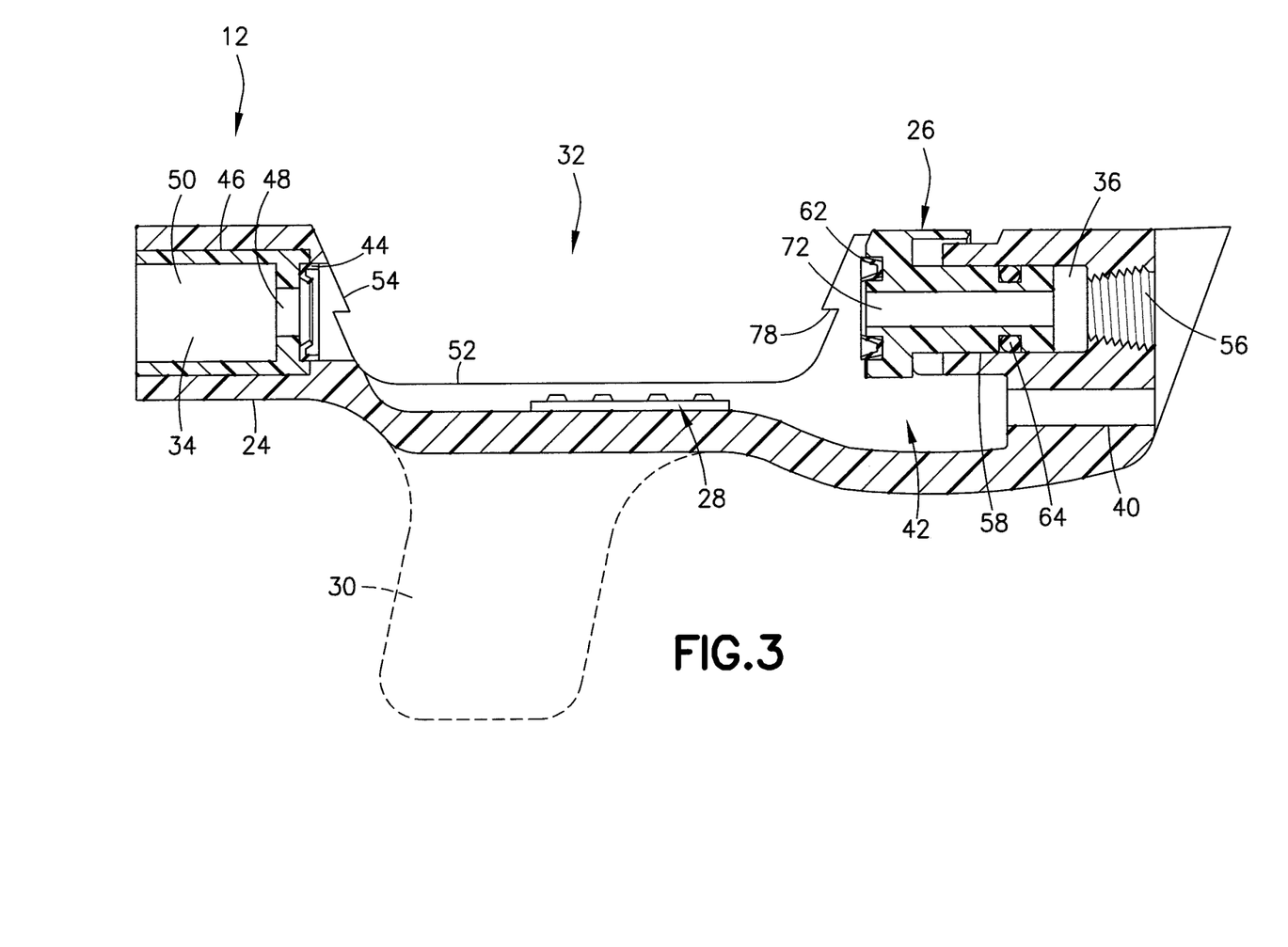
FIG. 3 is a schematic cross sectional view of the handpiece assembly shown in FIG. 2.

Referring also to FIG. 3, the handpiece assembly 12 generally comprises a frame 24, a movable latch 26, and electrical contacts 28. The frame 24, in this example embodiment, comprises a one-piece member made of a plastic or polymer material which forms a user handle for holding the apparatus 10. FIGS. 2 and 3 illustrate that the user handle may comprises a pistol grip type extension 30 from the bottom side of the frame 24. However, the pistol grip type extension 30 might not be provided as illustrated by FIG. 1. The frame 24, in this example embodiment, comprises a motor receiving area 32, a first aperture 34 and a second aperture 36. The motor receiving area 32 is sized and shaped to removably received the cannulated motor assembly 14 therein. The first aperture 34 extends through the frame 24 between the distal end of the frame and the motor receiving area 32. The second aperture 36 extends through the frame 24 between motor receiving area 32 and the proximal end of the frame 24. The first aperture 34 and the second aperture 36 are coaxially aligned. The electrical contacts 28 are located at the bottom of the motor receiving area 32 in this example embodiment and have the electrical conductors of the cable 22 connected thereto. The electrical contacts 28 may comprise contact pads or spring contacts for example. A strain relief 38 may be provided at the channel 40 for the cable 22. Area 42 in the motor receiving area 32 may function as a cable bay for the electrical conductors leading to the electrical contacts 28.

In this example embodiment a first seal 44 is provided at the motor receiving area 32 proximate the first aperture 34. In this example the first seal 44 is mounted on a seal holder 46 which is fixedly mounted in the first aperture 34. The seal holder 46 has an aperture 48 to allow a portion of the cannulated motor assembly 14 to extend therethrough into the area 50. The area 50 forms a location to allow the proximal end of the surgical tool to be removably attached to the cannulated motor assembly 14. The first seal 44 is located relative to the cannulated motor assembly 14 to be able to form a seal with a proximal end of the cannulated motor assembly 14, surrounding the drive shaft of the cannulated motor assembly 14 extending through the aperture 48, when the cannulated motor assembly 14 is inserted into the motor receiving area 32. In the embodiment shown the first seal 44 is a lip seal. However, any suitable type of seal may be provided such as an O-ring for example.

The motor receiving area 32 is open on the top side of the frame 24 and, in this example embodiment, also substantially open on the lateral sides of the frame except for the side lips 52. The frame 24 has stationary latches 54 projecting rearward at the front end of the motor receiving area 32 at lateral sides of the frame 24. The second aperture 36 has a threaded portion 56 configured to has a suction hose fitting attached thereto. Another portion 58 of the second aperture 36 has a smooth bore.

Figure 4:
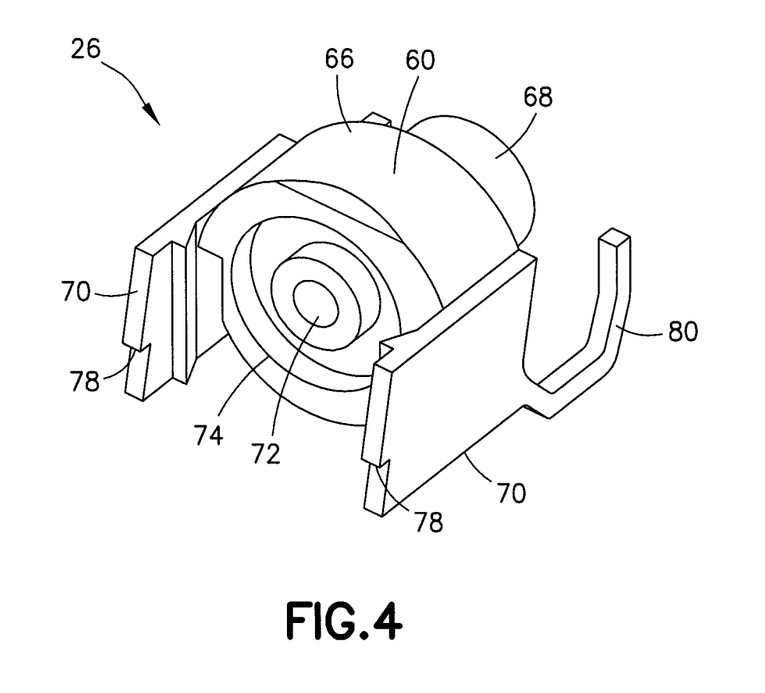
FIG. 4 is a perspective view of the movable latch shown in FIGS. 2-3.

Referring also to FIG. 4, the movable latch 26 generally comprises a frame 60, a second seal 62 and a third seal 64. The frame 60 is preferably a one-piece member comprised of plastic or polymer material. The frame 60 comprises a main section 66, an extension 68 extending from the main section 66, two lateral slides 70 on the main section 66, and a channel or conduit 72 extending through the main section 66 and the extension 68. The extension 68 is slideably located inside the smooth bore portion 58 of the second aperture 36. The third seal 64, such as an O-ring for example, is on the extension 68 and engages the smooth bore portion 58 of the second aperture 36. The second seal 62 is located at the proximal end of the frame 60, around the entrance to the channel 72, at groove 74. In the embodiment shown the second seal 62 is a lip seal. However, any suitable type of seal may be provided such as an O-ring for example. The second seal 62 is configured to engage the proximal end of the cannulated motor assembly 14 and form a seal between the latch 26 and the cannulated motor assembly 14 to contain the suction flow from the cannulated motor assembly 14 into the second aperture 36. The conduit 72 through the movable latch 26 is aligned with the second aperture 36 to allow flow from the cannulated motor assembly 14, through the conduit 72, through the second aperture 36, and out the suction conduit 20.

Bottom surfaces of the lateral slides 70 are located to slide on corresponding surfaces 76 of the frame 24 of the handpiece assembly 12. The front ends of the lateral slides 70 have latching surfaces 78. The rear ends of the lateral sides 70 have resilient cantilevered spring legs 80. The spring legs 80 engage a portion of the frame 24 to bias the movable latch in a forward direction on the frame 24. However, the movable latch 26 is configured to be resiliently moved out of the path of the cannulated motor assembly 14 while the cannulated motor assembly 14 is being inserted into the motor receiving area 32 and, by means of the spring legs resiliently deflecting, then subsequently snap back into its forward position, latching the cannulated motor assembly 14 in a fixed position in the motor receiving area 32. However, this is merely one example embodiment. In alternate example embodiments other types of latches and biasing means or springs could be provided.

Figure 5:
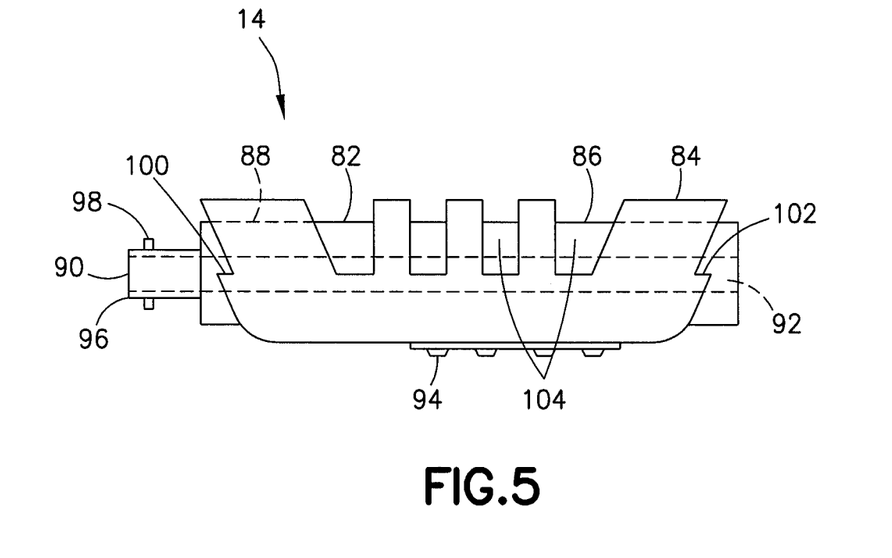
FIG. 5 is a perspective view of the cannulated motor assembly shown in FIG. 2.
Figure 6:
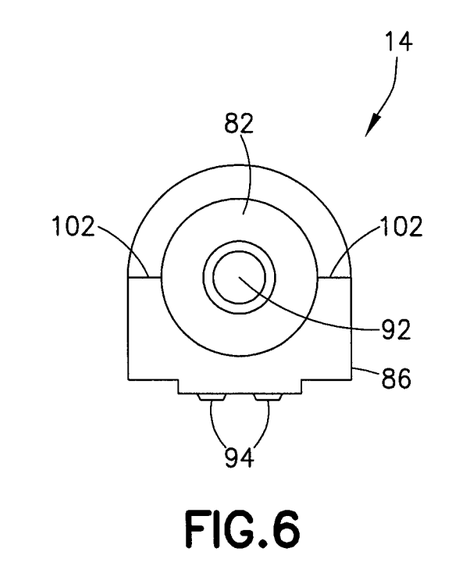
FIG. 6 is a rear end view of the cannulated motor assembly shown in FIG. 5.

Referring also to FIGS. 5-6, the cannulated motor assembly 14 generally comprises an electric motor 82 and a motor assembly housing 84. The motor 82 is a cannulated motor comprising a housing 86, a stator 88 and a rotor or drive shaft 90. The drive shaft 90 has a conduit or channel 92 therethrough along its longitudinal axis. The stator is configured to axially rotate the drive shaft 90 about it longitudinal axis. In an alternate example embodiment the motor could comprises a configuration to reciprocally move the drive shaft along a longitudinal axis. In this example embodiment the cannulated motor assembly 14 also comprises electrical contacts 94 on its bottom side. The drive shaft 90 has a distal end 94 with a mechanical connector 96 configured to have an end of the surgical tool 16 removable connected thereto. In this example the mechanical connector 96 comprises mounting pins.

The motor assembly housing 84 may be comprised of plastic or polymer material for example. In the example embodiment shown, the motor assembly housing 84 is removably attached to the electric motor 82 such that the motor assembly housing 84 may be disposed of after use. However, in an alternate example the motor assembly housing 84 might not be removably attached to the electric motor 82. In the example embodiment shown, the motor assembly housing 84 comprises first end latches 100 on a first end of the motor assembly housing 84 and second end latches 102 on an opposite second end of the motor assembly housing 84. Between the two ends of the motor assembly housing 84 cooling slots or holes 104 are provided through the motor assembly housing 84 proximate its top side which extend down along both lateral sides. These cooling slots or holes 104 allow heat to dissipate from the electric motor 82 at the top side of the apparatus 10.

As noted above, the cannulated motor assembly 14 is removably connected to the handpiece assembly 12. In this particular example embodiment, the first end of the cannulated motor assembly 14 having the connector 98 is inserted or slide into the motor receiving area 32, as indicated by arrow A in FIG. 2, with the distal end 96 of the drive shaft 90 extending into the aperture 34, 48. The first end latches 100 engage the stationary latches 54, and the cannulated motor assembly 14 is rotated down as indicated by arrow B in FIG. 2. The first seal 44 is able to engage the housing 86 of the motor 82 and form a seal around the distal end of the drive shaft.

As the cannulated motor assembly 14 is rotated down, the movable latch 26 is engaged by the motor assembly housing 84 which causes the movable latch 26 to be moved in the direction C as indicated in FIG. 2. The spring legs 80 are able to resiliently deflect during this movement C of the movable latch 26. The second end latches 102 then pass under the latch surfaces 78 of the movable latch 26 and, the spring legs 80 bias the movable latch 26 back to its forward position with the cannulated motor assembly 14 then being latched to the handpiece assembly 12 by the movable latch 26. The seal 62 on the movable latch 26 makes a sealing engagement with the housing 86 to seal between the channel 92 and the second aperture 36. The two sets of electrical contacts 28, 94 make electrical connection with one another to allow power and signals to be supplied to the cannulated motor assembly 14. Because the motor assembly housing 84 is wrapped around the top side and two lateral sides of the motor 82, the motor assembly housing 84 is able to removably retain the motor 82 in the motor receiving area 32.

After use of the apparatus 10, the connection process can be reversed with the user pulling on the movable latch 26 in direction C to disengage the movable latch 26 from the cannulated motor assembly 14, rotating the cannulated motor assembly 14 upward reverse to direction B, and pulling the cannulated motor assembly 14 out of the motor receiving area 32 reverse to direction A. The handpiece assembly 12 may then be disposed of, the motor assembly housing 84 may be disposed of, and the motor 82 may be cleaned for reuse with a new handpiece assembly 12 and new motor assembly housing 84.

An example embodiment may be provided in a medical device comprising a cannulated motor; and a handpiece, wherein the cannulated motor is configured to be detachably/releasably disposed within the handpiece (removable/disengagable from the handpiece).

An example embodiment may be provided in a medical device comprising a cannulated motor; and a handpiece having an open pocket/socket, wherein the handpiece is configured to detachably house/receive the cannulated motor in the open pocket/socket.

An example embodiment may be provided in a medical device comprising a handpiece; a cannulated motor; and a motor casing configured to (detachably/fixedly) hold/receive the cannulated motor, the motor casing configured to be detachably disposed within the handpiece, wherein the motor casing is configured to allow the cannulated motor to be in electrical communication with a power source.

An example embodiment may be provided in a medical device comprising a handpiece; a cannulated motor configured to be detachably disposed within the handpiece; and a retainer/coupler, wherein the retainer/coupler is configured to releasably secure the cannulated motor within the handpiece.

An example embodiment may be provided in a medical device comprising a handpiece; a cannulated motor; a motor casing configured to hold/receive the cannulated motor, the motor casing configured to be detachably disposed within the handpiece, and a retainer/coupler, wherein the retainer/coupler is configured to detachably secure the motor casing within the handpiece.

An example embodiment may be provided in a medical device comprising a cannulated motor; a handpiece configured to detachably house/receive the cannulated motor; and a surgical tool configured to be operably connected (detachably/fixedly) to the cannulated motor, wherein the cannulated motor is configured to drive the surgical tool when the cannulated motor is in electrical communication with a power source.

An example embodiment may be provided in an apparatus comprising: a frame, where the frame comprises a user handle, a motor receiving area, and a first aperture through the frame into the motor receiving area, where the motor receiving area is configured to removably receive a cannulated motor assembly therein; and a first seal located proximate the first aperture through the frame, where the first seal is configured to form a seal between the cannulated motor assembly and the frame when the cannulated motor assembly is in the motor receiving area.

The handle may extend from a bottom of the frame, where a top of the frame comprises an opening to insert the cannulated motor assembly through the top of the frame into the motor receiving area. The first aperture may be sized and shaped to have a drive shaft of cannulated motor assembly extend therethrough, where the first aperture is configured to allow connector pins on the drive shaft to pass through the first aperture into a debrider tool connection area of the frame. The frame may comprise a second aperture through the frame coaxially aligned with the first aperture to allow fluid to flow through the first aperture, a conduit of the cannulated motor assembly and out the second aperture. The apparatus may further comprise a movable latch on the frame proximate the motor receiving area, where the latch is configured to releasably retain the cannulated motor assembly in the motor receiving area. The movable latch may be spring biased towards a first position on the frame. The movable latch may comprise a conduit therethrough which is configured to be aligned with a conduit through a drive shaft of the cannulated motor assembly, when the cannulated motor assembly is inserted into the motor receiving area, where the movable latch may further comprise a second seal configured to form a seal with the cannulated motor assembly when the cannulated motor assembly is inserted into the motor receiving area. The movable latch may comprise a third seal forming a seal between the latch and a second aperture through the frame. The apparatus may further comprise electrical contacts on the frame proximate the motor receiving area, where the electrical contacts are configured to contact electrical contacts on the cannulated motor assembly when the cannulated motor assembly is inserted into the motor receiving area. The apparatus may further comprise a cannulated motor assembly removably connected to the frame, where a portion of a drive shaft of the cannulated motor assembly extends into the first aperture. A movable latch may releasably retains the cannulated motor assembly in the motor receiving area. Electrical contacts at the motor receiving area may make a removable electrical connection to electrical contacts on the cannulated motor assembly. A movable member may be provided between the frame and the cannulated motor assembly, where the movable member comprises a conduit therethrough, a second seal configured to seal the movable member to the frame, and a third seal configured to seal the movable member to the cannulated motor assembly, where the movable member is configured to allow fluid to flow from the cannulated motor assembly, through the movable member and out a second aperture through the frame. The movable member may be spring biased towards a first position on the frame.

An example embodiment may be provided in an apparatus comprising: a cannulated motor comprising a rotatable drive shaft, where the rotatable drive shaft comprises a conduit therethrough and a first end configured to removably connect a debrider tool thereto; and a motor assembly housing on the cannulated motor, where the motor assembly housing is configured to attach to a frame of a handpiece assembly, where the cannulated motor is configured to be removably inserted into a motor receiving area of the handpiece assembly with the motor assembly housing releasably retaining the cannulated motor with the handpiece assembly.

The motor assembly housing may comprise a first latch surface at a first end of the apparatus and a second latch surface at an opposite second end of the apparatus, where the first latch surface is configured to latch to the frame of the handpiece assembly and the second latch surface is configured to latch with a movable latch on the handpiece assembly. The motor assembly housing may comprise apertures therethrough configured to allow heat from the cannulated motor to transfer out of the apparatus. The apparatus may be configured to be inserted into a top opening of the handpiece assembly and form at least a portion of a top side of a debrider. A first end of the drive shaft may comprise a mechanical connector to releasably connect a debrider tool thereto. The cannulated motor may further comprise electrical contacts configured to make a releasable electrical connection to electrical contacts on the handpiece assembly.

An example embodiment may be provided in a medical device comprising: a handpiece assembly; and an apparatus as described above removably connected to the handpiece assembly, where the handpiece assembly comprises: a frame, where the frame comprises a user handle, a motor receiving area, and a first aperture through the frame into the motor receiving area, where the motor receiving area has the apparatus removably located therein; and a first seal located on the frame proximate the first aperture, where the first seal forms a seal between the cannulated motor and the frame.

An example method may comprise: providing a frame comprising a user handle, a motor receiving area, and a first aperture through the frame into the motor receiving area, where the motor receiving area is configured to removably receive a cannulated motor assembly therein; and connecting a first seal to the frame proximate the first aperture, where the first seal is configured to form a seal between the cannulated motor assembly and the frame when the cannulated motor assembly is in the motor receiving area.

A top of the frame may comprise an opening to insert the cannulated motor assembly through the top of the frame into the motor receiving area, and where the seal is connected to the frame with insertion through the opening. The providing of the frame may comprise the frame including a second aperture through the frame, coaxially aligned with the first aperture, to allow fluid to flow through the first aperture, a conduit of the cannulated motor assembly and out the second aperture. The method may comprise connecting a movable latch on the frame proximate the motor receiving area, where the latch is configured to releasably retain the cannulated motor assembly in the motor receiving area. The movable latch may be spring biased towards a first position on the frame. The movable latch may comprise a conduit therethrough which is configured to be aligned with a conduit through a drive shaft of the cannulated motor assembly when the cannulated motor assembly is inserted into the motor receiving area, and where the movable latch further comprises a second seal configured to form a seal with the cannulated motor assembly when the cannulated motor assembly is inserted into the motor receiving area. The movable latch may comprise a third seal forming a seal between the latch and a second aperture through the frame. The method may further comprise connecting electrical contacts on the frame proximate the motor receiving area, where the electrical contacts are configured to contact electrical contacts on the cannulated motor assembly when the cannulated motor assembly is inserted into the motor receiving area. The method may further comprise removably connecting the cannulated motor assembly to the frame, where a portion of a drive shaft of the cannulated motor assembly extends into the first aperture.

An example method may comprise: providing a cannulated motor, where the cannulated motor comprises a drive shaft having a conduit therethrough and a connector at a first end of the drive shaft configured to removably connect a debrider tool thereto; and providing a motor assembly housing on the cannulated motor; where the motor assembly housing comprises a latch configured to be contacted by a latch of a handpiece to releasably mount the motor assembly housing, with the cannulated motor, in a receiving area of the handpiece. The method may further comprise connecting electrical contacts to the cannulated motor to allow the cannulated motor to make a removable electrical connection with electrical contacts in the receiving area of the handpiece.

An example method may comprise: providing a handpiece, where the handpiece comprises a frame forming a motor receiving area, where the frame comprises a first aperture through the frame into the motor receiving area, and where the frame comprises a user handle; and inserting a cannulated motor assembly into the motor receiving area, where a seal is provided between the cannulated motor assembly and the handpiece, and where the cannulated motor assembly is removably retained to the handpiece by a movable latch. The inserting of the cannulated motor assembly into the motor receiving area may comprise inserting of the cannulated motor assembly into a top opening of the frame of the handpiece such that the cannulated motor assembly forms at least a portion of a top side of a medical device. The providing of the handpiece may comprise providing a movable latch on the frame, where the inserting of the cannulated motor assembly into the motor receiving area comprises the latch latching onto the cannulated motor assembly to releasably retain the cannulated motor assembly in the motor receiving area. The latch may comprise a second seal and a third seal on the movable latch and the movable latch comprises conduit therethrough, where the conduit through the latch aligns with a conduit through a drive shaft of the cannulated motor assembly when the cannulated motor assembly is inserted into the motor receiving area, where the second seal forms a seal with the cannulated motor assembly when the cannulated motor assembly is inserted into the motor receiving area, and where the third seal forms a seal with the frame at a second aperture through the frame. The providing of the handpiece may comprise the frame of the handpiece including electrical contacts in the motor receiving area, and the inserting of the cannulated motor assembly into the motor receiving area comprises electrical contacts on the cannulated motor assembly making a removable electrical connection with the electrical contacts on the frame.

With one example embodiment a design may be provided wherein the handpiece has two major components namely: a handpiece assembly and a cannulated motor assembly. The handpiece may be a fully disposable assembly that is composed of a receiver housing that contains the sealing features for the cannulated motor on front and back. This may be an off-the-shelf lip seal or a static O-ring for example. It may have custom designed electrical contact pads to connect the motor signal and power supply once the cannulated motor is loaded. It may have a connection for the electrical cable with strain relief, and a space for those cables to be routed. It may have a threaded connection for an off-the shelf suction connector that is in-line axially with the cannulated motor hollow shaft and lastly, it may have an integrated spring loaded latch that retracts to accept, and return and reset to retain the motor.

The latch may have a seal groove and a suction path that is also axially aligned to the motor's hollow shaft. This latch may be a one-piece design that may snap over the housing and self-retain during assembly.

The cannulated motor may be a stand-alone motor assembly that is inserted into a disposable non-metallic housing, such as a PEEK material for example. The motor assembly may be fully re-usable by the process of CDS—cleaning, disinfecting and sterilizing. Sterilizable motors usually are certified by their manufacturers and capable of going through an autoclave (pressurizing and heating) for 500-800 cycles. The disposable motor housing may incorporate the termination to the electrical contact for the motor signals and power supply. The design may incorporate an open rib design on top to dissipate heat coming from the motor. This non-metallic housing can be a component of the disposable package and the motor can slide into this housing for use. It may self-align itself once assembled or loaded in place to the handpiece assembly. The hollow shaft may have a pin design to accept blade engagement for rotation or oscillating function. After use, the motor and motor housing can be removed by releasing the latch by pulling it to the rear and, thus, unlatching the motor housing and will be reprocessed for cleaning, disinfecting and sterilizing. The one time use handpiece housing assembly with the cable and tubesets and motor housing may then be discarded.

An example embodiment may be provided in an apparatus comprising: a frame, where the frame comprises a user handle, a motor receiving area, and a first aperture through the frame into the motor receiving area, where the motor receiving area is configured to removably receive a cannulated motor assembly therein; and a first seal located proximate the first aperture through the frame, where the first seal is configured to form a seal between the cannulated motor assembly and the frame when the cannulated motor assembly is in the motor receiving area.

The handle may extend from a bottom of the frame, and a top of the frame may comprise an opening to insert the cannulated motor assembly through the top of the frame into the motor receiving area. The first aperture may be sized and shaped to have a drive shaft of cannulated motor assembly extend therethrough, where the first aperture may be configured to allow connector pins on the drive shaft to pass through the first aperture into a debrider tool connection area of the frame. The frame may comprise a second aperture through the frame coaxially aligned with the first aperture to allow fluid to flow through the first aperture, a conduit of the cannulated motor assembly and out the second aperture. The apparatus may further comprise a movable latch on the frame proximate the motor receiving area, where the latch is configured to releasably retain the cannulated motor assembly in the motor receiving area. The movable latch may be spring biased towards a first position on the frame. The movable latch may comprise a conduit therethrough which is configured to be aligned with a conduit through a drive shaft of the cannulated motor assembly when the cannulated motor assembly is inserted into the motor receiving area, and where the movable latch may further comprise a second seal configured to form a seal with the cannulated motor assembly when the cannulated motor assembly is inserted into the motor receiving area. The movable latch may comprise a third seal forming a seal between the latch and a second aperture through the frame. The apparatus may further comprise electrical contacts on the frame proximate the motor receiving area, where the electrical contacts are configured to contact electrical contacts on the cannulated motor assembly when the cannulated motor assembly is inserted into the motor receiving area. The apparatus may further comprise a cannulated motor assembly removably connected to the frame, where a portion of a drive shaft of the cannulated motor assembly extends into the first aperture. A movable latch may releasably retain the cannulated motor assembly in the motor receiving area. Electrical contacts at the motor receiving area may make a removable electrical connection to electrical contacts on the cannulated motor assembly. A movable member may be provided between the frame and the cannulated motor assembly, where the movable member comprises a conduit therethrough, a second seal configured to seal the movable member to the frame, and a third seal configured to seal the movable member to the cannulated motor assembly, where the movable member is configured to allow fluid to flow from the cannulated motor assembly, through the movable member and out a second aperture through the frame. The movable member may be spring biased towards a first position on the frame.

An example embodiment may be provided in an apparatus comprising: a cannulated motor comprising a rotatable drive shaft, where the rotatable drive shaft comprises a conduit therethrough and a first end configured to removably connect a debrider tool thereto; and a motor assembly housing on the cannulated motor, where the motor assembly housing is configured to attach to a frame of a handpiece assembly, where the cannulated motor is configured to be removably inserted into a motor receiving area of the handpiece assembly with the motor assembly housing releasably retaining the cannulated motor with the handpiece assembly.

The motor assembly housing may comprise a first latch surface at a first end of the apparatus and a second latch surface at an opposite second end of the apparatus, where the first latch surface is configured to latch to the frame of the handpiece assembly and the second latch surface is configured to latch with a movable latch on the handpiece assembly. The motor assembly housing may comprise apertures therethrough configured to allow heat from the cannulated motor to transfer out of the apparatus. The apparatus may be configured to be inserted into a top opening of the handpiece assembly and form at least a portion of a top side of a debrider. A first end of the drive shaft may comprise a mechanical connector to releasably connect a debrider tool thereto. The cannulated motor may further comprise electrical contacts configured to make a releasable electrical connection to electrical contacts on the handpiece assembly.

An example method may comprise: providing a frame comprising a user handle, a motor receiving area, and a first aperture through the frame into the motor receiving area, where the motor receiving area is configured to removably receive a cannulated motor assembly therein; and connecting a first seal to the frame proximate the first aperture, where the first seal is configured to form a seal between the cannulated motor assembly and the frame when the cannulated motor assembly is in the motor receiving area.

A top of the frame may comprise an opening to insert the cannulated motor assembly through the top of the frame into the motor receiving area, and where the seal may be connected to the frame with insertion through the opening. The providing of the frame may comprise the frame including a second aperture through the frame, coaxially aligned with the first aperture, to allow fluid to flow through the first aperture, a conduit of the cannulated motor assembly and out the second aperture. The method may further comprise connecting a movable latch on the frame proximate the motor receiving area, where the latch may be configured to releasably retain the cannulated motor assembly in the motor receiving area. The movable latch may be spring biased towards a first position on the frame. The movable latch may comprise a conduit therethrough which is configured to be aligned with a conduit through a drive shaft of the cannulated motor assembly when the cannulated motor assembly is inserted into the motor receiving area, and where the movable latch may further comprise a second seal configured to form a seal with the cannulated motor assembly when the cannulated motor assembly is inserted into the motor receiving area. The movable latch may comprise a third seal forming a seal between the latch and a second aperture through the frame. The method may further comprise connecting electrical contacts on the frame proximate the motor receiving area, where the electrical contacts may be configured to contact electrical contacts on the cannulated motor assembly when the cannulated motor assembly is inserted into the motor receiving area. The method may further comprise removably connecting the cannulated motor assembly to the frame, where a portion of a drive shaft of the cannulated motor assembly may extend into the first aperture.

An example method may comprise: providing a cannulated motor, where the cannulated motor comprises a drive shaft having a conduit therethrough and a connector at a first end of the drive shaft configured to removably connect a debrider tool thereto; and providing a motor assembly housing on the cannulated motor; where the motor assembly housing comprises a latch configured to be contacted by a latch of a handpiece to releasably mount the motor assembly housing, with the cannulated motor, in a receiving area of the handpiece.

The method may further comprise connecting electrical contacts to the cannulated motor to allow the cannulated motor to make a removable electrical connection with electrical contacts in the receiving area of the handpiece.

An example method may comprise: providing a handpiece, where the handpiece comprises a frame forming a motor receiving area, where the frame comprises a first aperture through the frame into the motor receiving area, and where the frame comprises a user handle; and inserting a cannulated motor assembly into the motor receiving area, where a seal is provided between the cannulated motor assembly and the handpiece, and where the cannulated motor assembly is removably retained to the handpiece by a movable latch.

The inserting of the cannulated motor assembly into the motor receiving area may comprise inserting of the cannulated motor assembly into a top opening of the frame of the handpiece such that the cannulated motor assembly forms at least a portion of a top side of a medical device. The providing of the handpiece may comprise providing a movable latch on the frame, where the inserting of the cannulated motor assembly into the motor receiving area comprises the latch latching onto the cannulated motor assembly to releasably retain the cannulated motor assembly in the motor receiving area. The latch may comprise a second seal and a third seal on the movable latch and the movable latch may comprise conduit therethrough, where the conduit through the latch may align with a conduit through a drive shaft of the cannulated motor assembly when the cannulated motor assembly is inserted into the motor receiving area, where the second seal may form a seal with the cannulated motor assembly when the cannulated motor assembly is inserted into the motor receiving area, and where the third seal may form a seal with the frame at a second aperture through the frame. The providing of the handpiece may comprise the frame of the handpiece including electrical contacts in the motor receiving area, and the inserting of the cannulated motor assembly into the motor receiving area may comprise electrical contacts on the cannulated motor assembly making a removable electrical connection with the electrical contacts on the frame.

It should be understood that the foregoing description is only illustrative. Various alternatives and modifications can be devised by those skilled in the art. For example, features recited in the various dependent claims could be combined with each other in any suitable combination(s). In addition, features from different embodiments described above could be selectively combined into a new embodiment. Accordingly, the description is intended to embrace all such alternatives, modifications and variances which fall within the scope of the appended claims.

What is claimed is:

1. An apparatus comprising:
    a frame, where the frame comprises a user handle extending from a bottom of the frame, a motor receiving area, a first aperture through the frame into the motor receiving area, and electrical contacts on the frame proximate the motor receiving area, where the motor receiving area is configured to removably receive a cannulated motor assembly therein; and
    a first seal located proximate the first aperture through the frame, where the first seal is configured to form a seal between the cannulated motor assembly and the frame when the cannulated motor assembly is in the motor receiving area;
    where the frame comprises a motor assembly opening extending along a top side of the frame to allow for insertion of the cannulated motor assembly through the top side of the frame into the motor receiving area; and
    where the electrical contacts on the frame removably engage and make an electrical connection with electrical contacts on the cannulated motor assembly when the cannulated motor assembly is inserted into the motor receiving area.

2. The apparatus as in claim 1 where the first aperture is sized and shaped to have a drive shaft of the cannulated motor assembly extend therethrough, where the first aperture is configured to allow connector pins on the drive shaft to pass through the first aperture into a debrider tool connection area of the frame.

3. The apparatus as in claim 1 where the frame comprises a second aperture through the frame coaxially aligned with the first aperture to allow fluid to flow through the first aperture, a conduit of the cannulated motor assembly and out the second aperture.

4. The apparatus as in claim 1 further comprising a movable latch on the frame proximate the motor receiving area, where the movable latch is configured to releasably retain the cannulated motor assembly in the motor receiving area.

5. The apparatus as in claim 4 where the movable latch is spring biased towards a first position on the frame.

6. The apparatus as in claim 4 where the movable latch comprises a first conduit therethrough which is configured to be aligned with a second conduit through a drive shaft of the cannulated motor assembly when the cannulated motor assembly is inserted into the motor receiving area, and where the movable latch further comprises a second seal configured to form a seal with the cannulated motor assembly when the cannulated motor assembly is inserted into the motor receiving area.

7. The apparatus as in claim 6 where the movable latch comprises a third seal forming a seal between the movable latch and a second aperture through the frame.

8. The apparatus as in claim 1 further comprising a cannulated motor assembly removably connected to the frame, where a portion of a drive shaft of the cannulated motor assembly extends into the first aperture.

9. The apparatus as in claim 8 where a movable latch releasably retains the cannulated motor assembly in the motor receiving area.

10. The apparatus as in claim 8 where a movable member is provided between the frame and the cannulated motor assembly, where the movable member comprises a conduit therethrough, a second seal configured to seal the movable member to the frame, and a third seal configured to seal the movable member to the cannulated motor assembly, where the movable member is configured to allow fluid to flow from the cannulated motor assembly, through the movable member and out a second aperture through the frame.

11. The apparatus as in claim 10 where the movable member is spring biased towards a first position on the frame.

12. The apparatus as in claim 1 wherein the electrical contacts on the frame proximate the motor receiving area comprise contact pads.

13. The apparatus as in claim 1 wherein the electrical contacts on the frame proximate the motor receiving area comprise spring contacts.

14. An apparatus comprising:
a handpiece assembly including a frame and a movable latch, where the frame includes a motor receiving area and electrical contacts on the frame proximate the motor receiving area; and
a cannulated motor assembly including:
a cannulated motor comprising a rotatable drive shaft, where the rotatable drive shaft comprises a conduit therethrough and a first end configured to removably connect a debrider tool thereto; and
a motor assembly housing on the cannulated motor;
where the cannulated motor assembly is configured to be removably inserted into the motor receiving area of the frame with the motor assembly housing releasably retaining the cannulated motor with the handpiece assembly,
where the motor assembly housing comprises a first latch surface at a first end of the motor assembly housing and a second latch surface at an opposite second end of the motor assembly housing,
where the first latch surface is configured to latch to the frame of the handpiece assembly and the second latch surface is configured to latch with the movable latch on the handpiece assembly, and
where the electrical contacts on the frame removably engage and make an electrical connection with electrical contacts on the cannulated motor assembly when the cannulated motor assembly is inserted into the motor receiving area.

15. The apparatus as in claim 14 where the motor assembly housing comprises apertures therethrough configured to allow heat from the cannulated motor to transfer out of the apparatus.

16. The apparatus as in claim 14 where the apparatus is configured to be inserted into a top opening of the handpiece assembly and form at least a portion of a top side of a debrider.

17. The apparatus as in claim 14 where the first end of the rotatable drive shaft comprises a mechanical connector to releasably connect a debrider tool thereto.

18. The apparatus as in claim 14, where the frame further comprises a user handle and a first aperture through the frame into the motor receiving area, and where the handpiece assembly further comprises a first seal located on the frame proximate the first aperture, the first seal forming a seal between the cannulated motor and the frame.

19. An apparatus comprising:
a frame, where the frame comprises a user handle, a motor receiving area, and a first aperture through the frame into the motor receiving area, where the motor receiving area is configured to removably receive a cannulated motor assembly therein;
a first seal located proximate the first aperture through the frame, where the first seal is configured to form a seal between the cannulated motor assembly and the frame when the cannulated motor assembly is in the motor receiving area; and
a movable latch on the frame proximate the motor receiving area, where the movable latch is configured to releasably retain the cannulated motor assembly in the motor receiving area;
where the movable latch comprises a first conduit therethrough which is configured to be aligned with a second conduit through a drive shaft of the cannulated motor assembly when the cannulated motor assembly is inserted into the motor receiving area, and where the movable latch further comprises a second seal configured to form a seal with the cannulated motor assembly when the cannulated motor assembly is inserted into the motor receiving area.

20. The apparatus as in claim 19 where the movable latch comprises a third seal forming a seal between the movable latch and a second aperture through the frame.

* * * * *